(12) United States Patent
Kitagawa (10) Patent No.: US 7,810,392 B2
(45) Date of Patent: Oct. 12, 2010

(54) SYSTEM FOR MEASURING AGE ON BASIS OF PHYSICAL STRENGTH

(75) Inventor: Katsuyuki Kitagawa, Kaga (JP)

(73) Assignee: Yugenkaisha Japan Tsusyo (JP)

( * ) Notice: Subject to any disclaimer, the term of this patent is extended or adjusted under 35 U.S.C. 154(b) by 248 days.

(21) Appl. No.: 11/816,386

(22) PCT Filed: Feb. 15, 2005

(86) PCT No.: PCT/JP2005/002254

§ 371 (c)(1),
(2), (4) Date: Nov. 19, 2008

(87) PCT Pub. No.: WO2006/087767

PCT Pub. Date: Aug. 24, 2006

(65) Prior Publication Data

US 2009/0133492 A1    May 28, 2009

(51) Int. Cl.
*A61B 5/22* (2006.01)
(52) U.S. Cl. .................................. 73/379.01
(58) Field of Classification Search ............. 73/379.01; 600/300
See application file for complete search history.

(56) References Cited

U.S. PATENT DOCUMENTS 6,547,729 B1 * 4/2003 Abbo ...................... 600/300
6,569,624 B1 * 5/2003 Weindruch et al. ........... 435/6
7,273,453 B2 * 9/2007 Shallenberger ............. 600/300
2003/0060690 A1 * 3/2003 Jelliffe et al. ............... 600/300

FOREIGN PATENT DOCUMENTS

| JP | 5-13669 | 2/1993 |
| JP | 2828670 | 9/1998 |
| JP | 2001-29503 | 2/2001 |
| JP | 2004-81621 | 3/2004 |
| JP | 2004-278150 | 10/2004 |

OTHER PUBLICATIONS

Chisan Shuppan, "Field Athletic Nyumon", 1976, pp. 68, 69, 102-103, 113, 109 and 119.
Filed Athletic Kyokai, "Field Athletic News", No. 40, 1978.
Field Athletic Kyokai, "Field Athletic News", No. 123, 1985.

* cited by examiner

*Primary Examiner*—Jewel Thompson
(74) *Attorney, Agent, or Firm*—Lowe Hauptman Ham & Berner, LLP (57) ABSTRACT

A system for measuring a person's age on the basis of his/her physical strength is disclosed. A system is provided using multiple exercise courses that make a user perform various kinds of exercises without overburdening the user and that include entertainment factors. A user's age can be calculated, based on the amount of time that the user takes to complete each course and all of the courses taken together, on the basis of the physical strength of a user and the degree to which the user can perform various exercise movements. This system includes multiple courses, to which various exercise devices or other features are provided. The exercise courses are formed so that the user demonstrates various physical abilities, including muscle strength at multiple portions of his/her body, flexibility of the body, balance of the body, and agility of the body.

10 Claims, 10 Drawing Sheets

SYSTEM FOR MEASURING AGE ON BASIS OF PHYSICAL STRENGTH

CROSS-REFERENCE TO RELATED APPLICATIONS

The present Application is based on International Application No. PCT/JP2005/002254, filed Feb. 15, 2005 and priority is hereby claimed under 35 USC §119 based on this application. This application is hereby incorporated by reference in its entirety into the present application.

FIELD OF THE INVENTION

The present invention relates to a system, to be provided in a recreation facility, for measuring physical fitness, and more particularly relates to a system for measuring a user's age on a basis of physical strength, with the system (1) including various types of exercise courses that may have in them some elements of amusement so as to encourage the user to perform various exercises, and (2) being able to measure how long a user takes to progress through the exercises, so as to calculate the physical-strength age of the user and to assess which athletic activities the user is good or bad at.

BACKGROUND OF THE INVENTION

Conventionally, exercise equipment in a recreation facility is intended for young people who are physically fit and who have muscular strength, and thus is not suited for use by elderly people or children. Therefore, a health-factor measuring device that enables all members of a family, including elderly users, to take moderate exercise, and that also provides them with entertainment so that they can enjoy exercising, has been proposed (see Patent Document 1 below). With this health-factor measuring device, the time that each member of a family takes in completing a certain set of exercises can be measured, and the family members can enjoy comparing the amount of time that each member takes to complete the exercises and seeing who is the fastest in the family. This device, however, does not measure the age of a user on the basis of the user's physical strength.

In measuring the age of a student on the basis of the student's physical strength (e.g., an elementary, junior high, or high school student), the student is required to do simple, repetitive exercises, the performance of which is measured as follows: Instantaneous force is measured by the distance that the student jumps by a standing broad jump; grip strength is measured by a grip dynamometer; agility is measured by the number of sideways jumps that the student can do within a specified time; flexibility is measured by how much the student can bend forward when sitting on a floor with his/her legs extended to the front; endurance is measured by the number of sit-ups that the student can do within a specified time; balance is measured by how long the student can stand on one foot with his/her eyes open; and so on. In these measurements to assess age on the basis of physical strength, a user is made to do simple, repetitive exercises. Therefore, when performing such exercises, (1) the user does not have much fun; (2) the user is not made to perform complex muscle actions; (3) the user is not made to use muscles that he/she does not usually use; and (4) although the user's basic physical abilities are measured, the user's complex physical abilities, including memory, attention, and other functions of the brain, are not measured. Accordingly, the user is made to do a long series of a variety of exercises, and the user's physical-strength age is assessed by how long he/she takes to complete the series, and by comparing that time with time data obtained in advance. However, with this method, using a long series of exercises, it is not possible to assess which athletic activities the user is good or bad at.

Patent Document 1: Japanese Published Unexamined Patent Application No. 2001-29503

Patent Document 2: Japanese Published Unexamined Patent Application No. 2004-278150

SUMMARY OF THE INVENTION

The present invention has been made to solve the above-mentioned problems. One objective of the present invention is to provide a system for measuring age on the basis of physical strength, with the system (1) having multiple, varying exercise courses that may have in them some elements of amusement, so as to encourage the user to perform the various exercises comfortably and sufficiently, and (2) being able to measure how long a user takes to complete each exercise course as well as the entire series of courses, so as to calculate the age of the user on the basis of the user's physical strength and to assess how good or bad each of a user's exercise abilities is.

The present invention's system for measuring physical-strength age includes multiple exercise courses that include various types of exercise-related devices/features, with the exercise courses structured such that a user utilizes a variety of physical abilities, including muscle strength in multiple parts of his/her body, flexibility of the body, balance of the body, and agility of the body, the extent to which a user utilizes each of his/her various physical abilities is used as an index of the amount of the exercise performed, and the combination of the values of the indexes for each exercise course is different from the combination of values in each of the other exercise courses; the physical-strength age of a user is calculated based on the amount of time that the user takes to complete all of the exercise courses; and each of the various exercising abilities of the user is assessed based on the time that the user takes to complete each exercise course.

It is preferable that the specific exercises within each exercise course be arranged so that a user needs to memorize their order and specific features, and to use his/her judgment in selecting the posture or route to be taken in performing each exercise, with the result that intelligence is one of the indexes.

It is preferable that one exercise course (hereinafter "exercise course 1") have a passageway such that multiple logs having flat upper faces are horizontally or diagonally installed at a predetermined height above the ground (floor), and a structure, arranged in the middle of the passageway, that has a low ceiling that requires a user to change from a standing-upright posture to bending-down posture, a squatting posture, or an on-all-fours posture.

It is preferable that another exercise course (hereinafter "exercise course 2") be a meandering, upward-sloped passageway having a predetermined width and length, and that multiple projections or holes be provided on said passageway so as to make a user do one or more of the following: climbing up and jumping down; jumping over; crawling up and running down; or climbing while avoiding obstacles.

It is preferable that another exercise course (hereinafter "exercise course 3") includes a passageway that for most of its length includes two separate surfaces to be walked on (hereinafter "walking surfaces"), one for each of a user's legs, with each walking surface having a predetermined width, height, and length, and with the passageway such that in some portions one walking surface is higher than the other; that the passageway has one or more portions where the two walking surfaces are separated from each other (separated-walking-surfaces portion(s)), and one or more portions where the two walking surfaces converge into one (united-walking-surfaces portion(s)); and the separated-walking-surfaces portion(s) include one or more sections where the user can or must walk with his/her legs wide apart, as well as one or more sections where the two walking surfaces are of different heights, and one or more sections where the two walking surfaces have the same height.

It is preferable that another exercise course (hereinafter "exercise course 4") includes one passageway having a predetermined width, height, and length, with the passageway arranged so that it is winding from beginning to end; and it includes a portion where its walking surface goes up and down, a portion where the walking surface is horizontal, a portion where the walking surface is inclined to one side, and a portion where the walking surface is inclined on both sides, with the center of the walking surface being a boundary between the two sides.

It is preferable that another exercise course (hereinafter referred to as "exercise course 5") includes a meandering passageway that has a predetermined length and a center wall that divides the passageway; with the center wall provided with multiple through-holes into which a user can put his/her arms to support his/her body; and having an approximately vertical portion, an inclined portion, and a portion that is curved on both of its sides.

It is preferable that another exercise course (hereinafter "exercise course 6") includes a tunnel-shaped passageway in which inverted-U-shaped pipes are continuously arranged at predetermined intervals, with said pipes being of different heights, so that the passageway has a portion where the user can walk upright, a portion where the user must bend down in order to move forward, and a portion where the user must crouch in order to move forward; and inclined to the right or left so that the passageway has one or more portions where a user must bend his/her body to the right or left in order to move forward.

It is preferable that the exercise course (hereinafter "exercise course 7") be a passageway of a predetermined length, and that it be arranged such that it meanders up and down and to the right and left, and is equipped with two rails, one on the passageway's right side and one on the left side, with the rails arranged so that they sometimes are inclined upward and sometimes inclined downward, and sometimes are directed to the left and sometimes to the right, and metal fittings that are mounted to the rails and that slide forward and backward, and an interconnected series of hanging rings that are connected to the metal fittings.

It is preferable that said exercise courses be accommodated in a long dome made of polystyrene foam.

The present invention's system for measuring age on the basis of physical strength includes various types of exercise-related devices/features that are structured such that a user can demonstrate a variety of physical abilities, including muscle strength at multiple places of his/her body, flexibility of the body, balance of the body, and agility of the body; a method by which an index of the amount of exercise that a user performs is measured by the extent to which each of a user's physical abilities is demonstrated; exercise courses that each combine a unique set of exercises such that an index value for one exercise course is different from that for another exercise course; and various types of exercise exercise-related devices/features that differ from each other are installed for the purpose of creating different exercise courses.

As a result, a user's various exercise abilities can be assessed as good or bad according to calculations based on the amount of time that the user takes to complete each of the exercise courses, and the user's overall age on the basis of the user's physical strength can be calculated from the total amount of time that the user takes to complete all of the exercise courses.

Because the exercise courses are designed so that intelligence is included as an index and so that the intelligence index is given a larger value than the value for any other index, a user's brain functions, such as memory and judgment, are also be taken into consideration in calculating the user's age on the basis of the user's physical strength.

In exercise course 1, a user walks on logs, and the user must use his/her sense of balance to keep from falling down off of the logs. In addition, it is necessary for the user to use his/her leg muscles, such as the quadriceps femoris muscles and the gastrocnemial muscles. Flexibility of the body also is required. A user must also use his/her ability to quickly judge which posture is most suitable for a given movement, taking into consideration his/her physical strength. Index values representing agility or strength of arm muscles can be assigned small values, because what are assessed the most in this exercise course 1 are (a) the strength of leg muscles, and (b) flexibility of the body.

In exercise course 2, a user climbs up a slope on which there are obstacles, and therefore the index value for leg-muscle strength can be made large. The index values for balance, agility, and flexibility also must be given large values. In addition, a user is required to have the ability to judge a situation and decide whether to choose a sideways route where there are no obstacles even though doing that would take a longer time, or to go straight forward, climbing over large obstacles, even though he/she might stumble a few times along the way. If the user remembers the condition of an obstacle that he/she first climbs over—behind which holes are hidden—and stays careful afterwards, he/she will know that holes might also be hidden behind subsequent obstacles, and thus he/she can easily avoid the holes. And because the user also uses arm strength when climbing over the obstacles, the index for arm strength can be given a mid-level value.

Exercise course 3 has two walking surfaces and requires the user to walk with his/her legs apart, and therefore this facility particularly requires leg-muscle strength, though flexibility, agility, and balancing ability also are required. The user moves forward, placing his/her legs on the surfaces to be walked on in such a way that he/she rotates his/her legs and therefore uses inner-thigh muscles, such as the sartorius muscle and adducent muscles, that he/she does not usually use. In addition, such an exercise is said to be effective for preventing incontinence. Because it is hard for a person to remain standing for a long time with his/her legs apart, he/she needs to keep stepping forward quickly. Therefore, the index value for agility can be made large.

Exercise course 4 makes the user walk in a narrow passageway having a predetermined width, height, and length. Because the facility is formed such that the condition of the walking surface varies from place to place, the index value for bodily balance, among other values such as leg-muscle strength and flexibility, can be made large.

Exercise course 5 makes the user walk on a narrow passageway along a wall, and requires him/her to use his/her arms to support his/her body so as to keep from falling off the passageway, especially where said wall is inclined or curved toward the user. Accordingly, the index value for arm-muscle strength can be made large. The index values for flexibility and bodily balance also can be made large.

Exercise course 6 makes the user pass through an inverted-U-shaped pipe tunnel, some portions of which incline to the left or right. As a result, the index value for flexibility can be made large.

Exercise course 7 is a passageway constituted such that a user moves forward by using his/her hands to grip interconnected series of hanging rings. Where a rail is far from the user, this course is also suitable for a stretching exercise that requires a user to stretch his/her arms. As a result, the index values for flexibility and arm-muscle strength can be made high.

Because there are no columns in the long dome, there is nothing that might limit the shape or other features of each individual exercise course that is to be accommodated therein. And because the long dome can be extended, it can even accommodate a long exercise course. Furthermore, because the dome is not affected by weather conditions, the utilization rate of the exercise courses is not limited by weather conditions and hence can be high.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description thereof are to be regarded as illustrative in nature, and not as restrictive.

BRIEF DESCRIPTIONS OF THE DRAWINGS

Other characteristics and advantages of the invention will become apparent with the aid of the description which follows in conjunction with the appended drawings which represent.

EXPLANATION OF NUMBERS USED IN THE DRAWINGS

1 Log Range exercise course of the system for measuring age on the basis of physical strength

2 Climb of Grief exercise course of the system for measuring age on the basis of physical strength

3 Divided Pathway exercise course of the system for measuring age on the basis of physical strength

4 Road of Torsion exercise course of the system for measuring age on the basis of physical strength

5 Wall of Stagnation exercise course of the system for measuring age on the basis of physical strength

6 Cave of Bones exercise course of the system for measuring age on the basis of physical strength

7 Stretch with Hanging Rings exercise course of the system for measuring age on the basis of physical strength

8 Pipeline exercise course of the system for measuring age on the basis of physical strength

9 Air Forest exercise course of the system for measuring age on the basis of physical strength

10 Corridor of Mirrors exercise course of the system for measuring age on the basis of physical strength

11 Road of Reaching Out exercise course of the system for measuring age on the basis of physical strength 12 Suspension Bridge of Courage exercise course named of the system for measuring age on the basis of physical strength
15 user
20 diagram showing the arrangement of the exercise courses of the system for measuring age on the basis of physical strength
30 passageway
31 log
32 supporting pillar
40 upward-sloping pathway
41-43 obstacles
44 hole
50 pathway
51, 52 split walking surfaces
60 one-track pathway
70 pathway
71 central wall
72 through-hole
80 tunnel-shaped pathway
81 pipe
90 pathway
91, 92 rails
93, 94 metal fittings
95, 96 interconnected series of hanging rings
97 staircase
100 long dome
110 starting point
120 ending point
130 arch
S20-S27 procedure for using the system for measuring age on the basis of physical strength

DETAILED DESCRIPTION OF THE INVENTION

The present invention's system for measuring age on the basis of physical strength will now be explained in detail with reference to the drawings.

Figure 1:
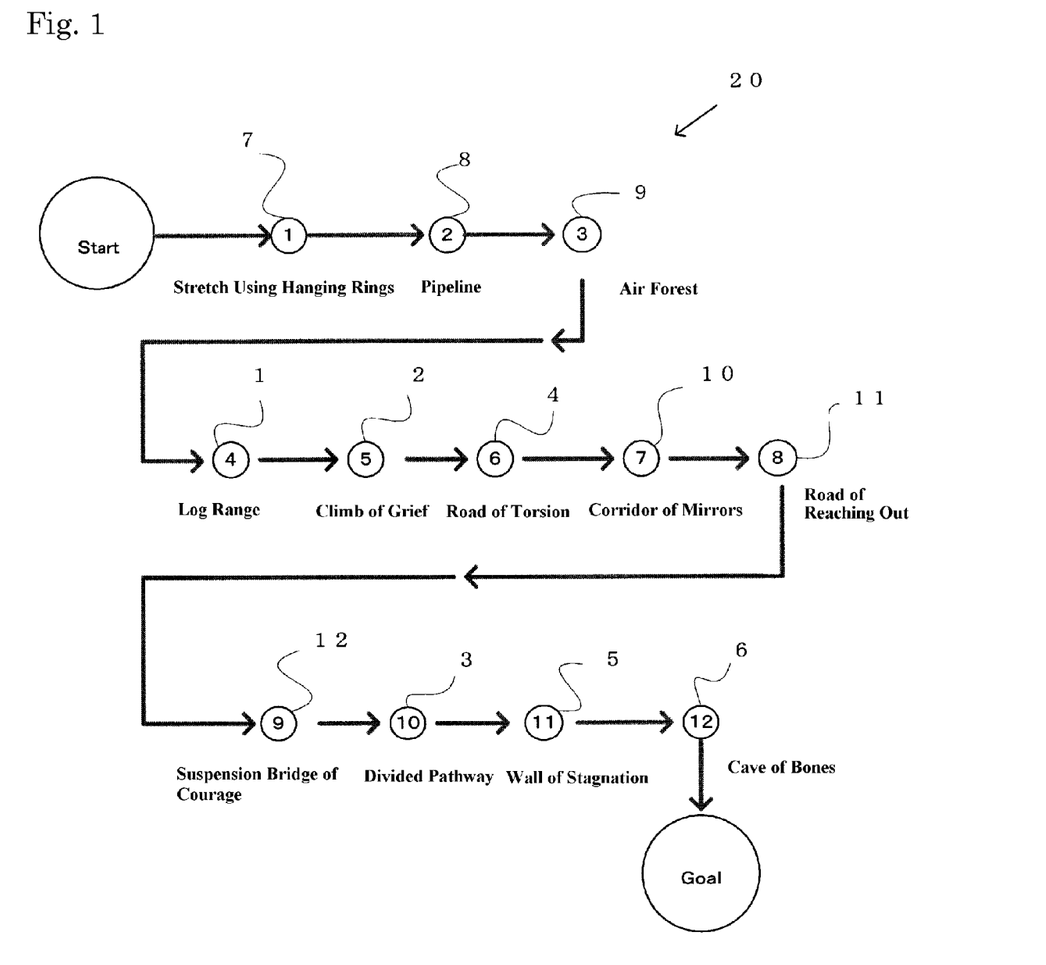
FIG. 1 is a diagram showing the arrangement of the exercise courses according to one embodiment of the present invention's system for measuring age on the basis of physical strength.

FIG. 1 shows the arrangement of the exercise courses according to one embodiment of the present invention's system for measuring age on the basis of physical strength. This system for measuring age on the basis of physical strength is set up as an outdoor facility. However, all of the exercise courses can be accommodated in a facility having a roof or in an indoor facility. As shown in diagram 20, which illustrates the arrangement of the system's courses, this embodiment of the physical-strength-age measuring system is comprised of 12 courses (each of which is represented by a circled number). Each course is designed such that a user can demonstrate a variety of physical abilities; a user proceeds through a series of courses while performing exercise-like movements, and the completion time thereof is calculated. The number of courses is not limited to 12, and the design of the courses can vary depending on what type and how many physical abilities are to be measured.

Each course has a unique name. Course 1 is named Stretch with Hanging Rings 7, which requires a user to walk while stretching his/her arms holding in each hand an interconnected series of hanging rings. Course 2 is named Pipeline 8, which requires a user to pass through a jungle of pipes. Course 3 is named Air Forest 9, which requires a user to push through large rubber balls in order to move forward. Course 4 is named Log Range 1, which requires a user to walk on logs while keeping his/her balance. Course 5 is named Climb of Grief 2, which requires a user to climb up a slope that has many obstacles. Course 6 is named Road of Torsion 4, which requires a user to walk along a narrow pathway. Course 7 is named Corridor of Mirrors 10, which requires a user to climb up a labyrinth-like arrangement of stairs. Course 8 is named Road of Reaching Out, which requires a user to walk along a pathway of pipes, while holding on to handrails. Course 9 is named Suspension Bridge of Courage 12, which requires a user to walk across a suspension bridge. Course 10 is named Divided Pathway 3, which requires a user to walk with his/her legs apart. Course 11 is named Wall of Stagnation 5, which requires a user to walk sideways, holding on to a wall. Course 12 is named Cave of Bones 6, which requires a user to move through a tunnel with his/her body in a contracted position.

In this embodiment, exercise course 1 is Log Range 1, exercise course 2 is Climb of Grief 2, exercise course 3 is Divided Pathway 3, exercise course 4 is Road of Torsion 4, exercise course 5 is Wall of Stagnation 5, exercise course 6 is Cave of Bones 6, and exercise course 7 is Stretch with Hanging Rings 7. These courses are mainly explained here. How long it takes for a user to complete one course varies from several tens of seconds to several minutes. However, the exercise facilities are designed such that a user can complete each course in about one minute. Therefore, in a case where there are 12 courses in total, a user can finish the entire series of courses in about 12 minutes, and even if the time for a user to go from one course to another is taken into consideration, the user can finish the entire series of courses in about 30 minutes. Exercising in such courses enables the stamina of a user to be measured. Also, each course is designed such that it requires a user to demonstrate the instantaneous force of his/her muscles, which is as important as stamina.

Figure 2:
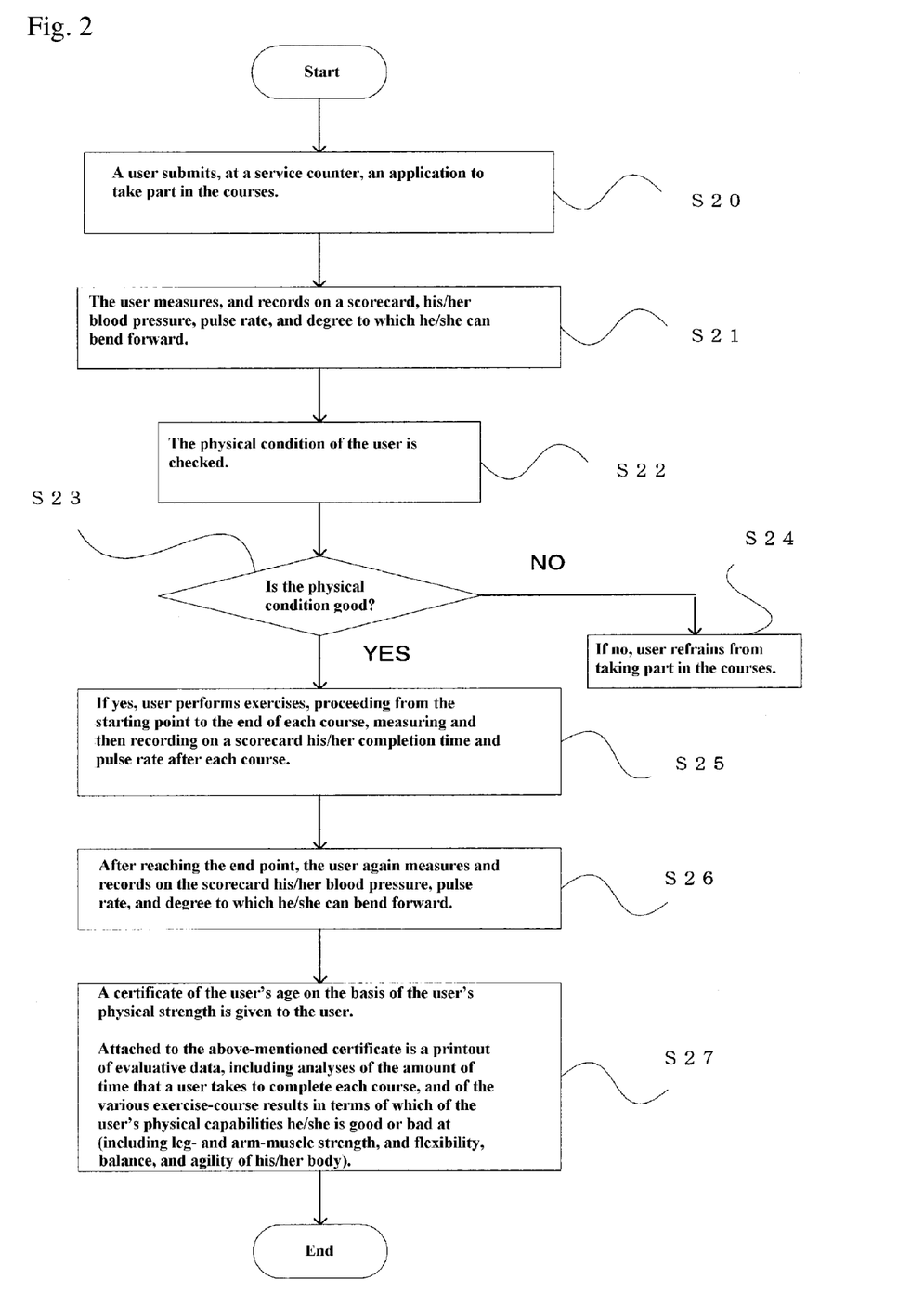
FIG. 2 is a flow chart showing the procedure for using the present invention's system for measuring age on the basis of physical strength.

FIG. 2 is a flow chart showing the procedure for using the system for measuring age on the basis of physical strength. As shown in FIG. 2, a user first submits at a service counter (S20) an application to use the system for measuring age on the basis of physical strength. Next, the user measures his/her blood pressure and pulse rate. Then, the user bends down forward on a pedestal or under a condition of staying long on a floor, to determine—and then record on a scorecard (memo pad)—the distance by which the tips of his/her fingers go below or over his/her toes (S21). Then the user's physical condition is checked (S22). For example, a user whose blood pressure is high or whose physical condition is not good (S23) is instructed to refrain from exercising in this course. (S24).

Each user is then given a stopwatch and a pulse meter. The user then proceeds through each course, and records on the above-mentioned scorecard how much time is necessary for the user to complete each course; the user also records his/her pulse rates when starting and finishing each course. The pulse meter also serves to help ensure that the user refrains from exercising excessively. When the user reaches the end of the series of courses, he/she again measures his/her blood pressure, pulse rate, and bending-forward distance, and records those numbers on the scorecard. Here, the user can realize that completing the 30-minute series of exercise courses has improved his/her ability to bend forward. Also, by considering the beginning and ending pulse rates, the user can tell whether he/she has been exercising enough. After the user writes down his/her actual age on the scorecard and submits the scorecard at the service counter, the scorecard is analyzed and the user's age on the basis of the user's physical strength is calculated and then printed on a certificate that is given to the user. The user is also informed as to which of his/her physical abilities are good or bad.

The system for calculating a user's age on the basis of the user's physical strength can be created using a personal computer (PC), for example. Also, data regarding past users are stored in the personal computer, and the statistical relationship between the time required for a user to complete all the courses and his/her actual age is updated each time that the user completes the series of courses. After the user's completion time for each course is entered, the age on the basis of the physical strength is calculated with reference to this statistical data.

Physical-strength age is calculated taking into consideration the time that a user takes in completing the entire series of courses. However, age on the basis of physical strength can also be calculated by the time that the user takes in completing any one of the courses. In either case, the age on the basis of the physical strength data is stored. An example of Wall of Stagnation 5 (exercise course 5) data in Course 11 is shown in Table 1, and an example of Cave of Bones 6 (exercise course 6) data in Course 12 is shown in Table 2. Age is classified according to 10-year groupings, but the classification period can be smaller. The style of these tables can be used for a table that shows the age of a user on the basis of the physical strength as calculated by taking into consideration the time needed to complete the entire series of courses.

TABLE 1

|   | Completion Time | Physical-Strength Age |
|---|---|---|
| 1 | 32 seconds | Teens |
| 2 | 36 seconds | 20s |
| 3 | 41 seconds | 30s |
| 4 | 53 seconds | 40s |
| 5 | 62 seconds | 50s |
| 6 | 70 seconds | 60s |
| 7 | 75 seconds | 70s |
| 8 | 82 seconds | 80s |

TABLE 2

|   | Completion Time | Physical-Strength Age |
|---|---|---|
| 1 | 15 seconds | Teens |
| 2 | 16 seconds | 20s |
| 3 | 21 seconds | 30s |
| 4 | 28 seconds | 40s |
| 5 | 32 seconds | 50s |
| 6 | 36 seconds | 60s |
| 7 | 40 seconds | 70s |
| 8 | 45 seconds | 80s |

In this embodiment, the following five physical abilities are evaluated: leg strength, arm strength, flexibility of the body, balance of the body, and agility of the body. Also, six indexes—indexes for the above-mentioned physical abilities, as well as an index for intelligence—are used. This embodiment evaluates, from among the muscles at various parts of the body, the strength of arm and leg muscles. However, this embodiment is not limited to evaluating the strength of legs and arms, and the strength of muscles in the hands, abdomen, and so on also can be evaluated. Moreover, a particular muscle at a specific portion of the legs can be focused on. With regard to leg strength, the focus can be either on a muscle that excels at endurance or on a muscle that excels at short periods of exertion of muscle force. The extent to which a muscle to be evaluated exerts strength is indexed as the amount of exercise, and the exercise courses are designed in such a way that one exercise course requires a different amount of exercise than that required by another exercise course. If the body is considered in more detail so as to decide which specific muscle(s) should be evaluated for muscle strength, an increased number of exercise courses will be necessary to evaluate the strength of each designated muscle, resulting in a more complicated overall exercise facility.

Usually, muscles are strengthened by using them. When muscles are exercised, they become thick and hard, but they lose flexibility. For this reason, when evaluating muscle strength, such ambivalent characteristics of muscles—with regard to the relation between their thickness/hardness and flexibility—are also taken into consideration. In addition, mental factors—such as memory, attention, and judgment, which are said to deteriorate as one ages—are added as an index. For example, by making a user judge which route is the shortest, or by presenting a device in which a door opens after a certain multi-digit number is memorized and entered by the user, the user's physical abilities, including his/her brain functions can be evaluated. If the amount of brain activity is counted as an amount of exercise, judgment is regarded as an exercising capability. If one's judgment is excellent, it manifests as quickness (i.e., short time taken in judging), and if judgment is poor, it manifests as slowness (i.e., long time taken in judging).

In this embodiment, for each type of exercise course, the following are indexed as measurements of exercise: physical abilities (i.e., leg strength, arm strength, flexibility of the body, balance of the body, and agility of the body), and the extent to which intelligence is demonstrated. The exercise courses are designed so that these indexes differ among the exercise courses. The amount of exercise corresponds to a workload, such as—in the case of the legs, for example—the amount of exercise in moving the legs up and down 10 times. If this amount of exercise is expressed as an index value of 10, an index value of 5 for the legs indicates one-half of the amount of exercise of an index value of 10. When this amount of exercise is divided by the muscle strength of the leg, the time taken to perform that amount of exercise can be determined. This can be expressed in the formula W/F=t (where W is the amount of exercise, F is the strength of a muscle, and t is the time taken to perform that amount of exercise). If 1/F is expressed as x, the above formula can be expressed as W·x=t.

If in an exercise course a user is made to perform the exercise amount W, and if the completion time t is measured, an inverse number x of the muscle strength can be calculated. Here, if the exercise course requires that a user do only one simple exercise, the simple exercise may not have in it any amusing or interesting elements. Therefore, if an exercise course is designed to make a user do three different exercises (e.g., exercises of the legs, hands, and abdomen), the number of muscle types to be evaluated increases, and thus the number of invert numbers of muscle strengths, namely variables to be determined, increases to three (i.e., x1, x2, and x3). In this case, a completion time t1 for this exercise course can be expressed as W1·x1+W2·x2+W3·x3=t1. If only one exercise course is completed, x1, x2, and x3 cannot be determined. Thus, when three variables are to be determined, three exercise courses, for example, can be provided. Then the exercise courses are designed so that an exercise amount W of one exercise course is different from the exercise amount W of another exercise course. If the completion times t1, t2, t3 for the three exercise courses are measured, the following three formulas are obtained: W11·x1+W12·x2+W12·x3=t1; W21·x1+W22·x2+W22·x3=t2; and W31·x1+W32·x2+W32·x3=t3. These are simultaneous linear equations, and therefore it is possible to determine x1, x2, and x3.

Table 3 shows the amounts of exercise (shown as indexes) to be performed ins exercise courses 1 to 7—namely Log Range 1, Climb of Grief 2, Divided Pathway 3, Road of Torsion 4, Wall of Stagnation 5, Cave of Bones 6, and Stretch with Hanging Rings 7. As shown in the table, the combination of indexes (for leg strength, arm strength, flexibility, balance, agility, and intelligence) is designed to differ among the various exercise courses. The various types of exercise and various course conditions are designed so that each physical ability can be evaluated by measuring the completion time for each exercise course. Also, Stretch with Hanging Rings is first of the courses, and it serves also as a warm-up course for loosening up the muscles of the body. In the case of the 12 courses, each of which involves the use of different exercise devices/features or different exercise conditions, the number of physical abilities that can be distinguished from each other is, in theory, 12.

TABLE 3

| Course | Legs | Arms | Flexibility | Balance | Agility | Intelligence |
|---|---|---|---|---|---|---|
| Log Range | 6 | 4 | 9 | 10 | 4 | 6 |
| Climb of Grief | 7 | 6 | 6 | 6 | 8 | 6 |
| Divided Pathway | 7 | 2 | 9 | 9 | 9 | 2 |
| Road of Torsion | 7 | 3 | 6 | 10 | 5 | 3 |
| Wall of Stagnation | 4 | 8 | 7 | 7 | 4 | 4 |
| Cave of Bones | 4 | 5 | 10 | 7 | 4 | 4 |
| Stretch with Hanging Rings | 4 | 6 | 10 | 3 | 5 | 2 |

Figure 3:
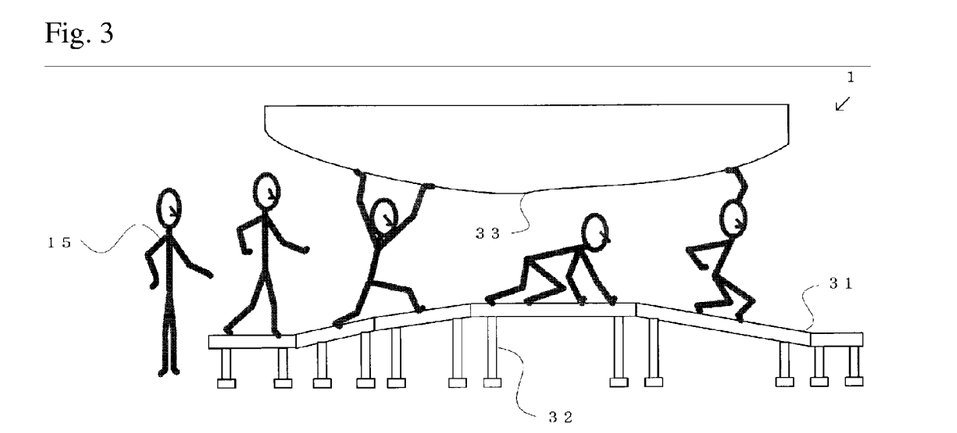
FIG. 3 is a side view of the Log Range exercise course of the present invention's system for measuring age on the basis of physical strength.
Figure 4:
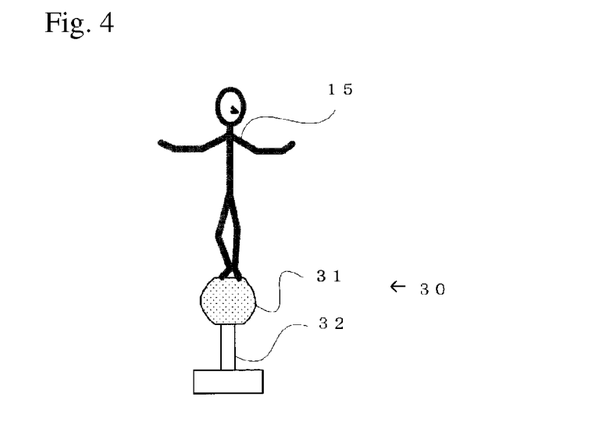
FIG. 4 is a cross sectional view of the Log Range exercise course of the present invention's system for measuring age on the basis of physical strength.

Among the 12 courses of the system for measuring age on the basis of physical strength, the exercise courses shown in Table 3 will now be described in more detail. FIG. 3 is a side view of the Log Range 1 exercise course. As shown by FIG. 3, this exercise course is a passageway 30, in which multiple logs 31 with flattened tops are horizontally or diagonally provided on supporting pillars at predetermined heights from the ground 32. In the middle of the passageway 30, a user-height-limiting board 33 is hung from the ceiling. Therefore, in order to move forward, a user must change his/her posture from a standing posture to a bent-down posture with his/her waist bent, a crouching posture with his/her legs bent, or an on-all-fours posture. If the user does not promptly judge which posture to take, the time needed to complete the course becomes longer. FIG. 4 is a cross sectional view of Log Range 1. Because the top surface of the log 31 is narrow, the user 15 needs to keep his/her balance while walking forward. If the user loses balance and falls from the log 31, the time needed to complete the course becomes accordingly longer.

Figure 5:
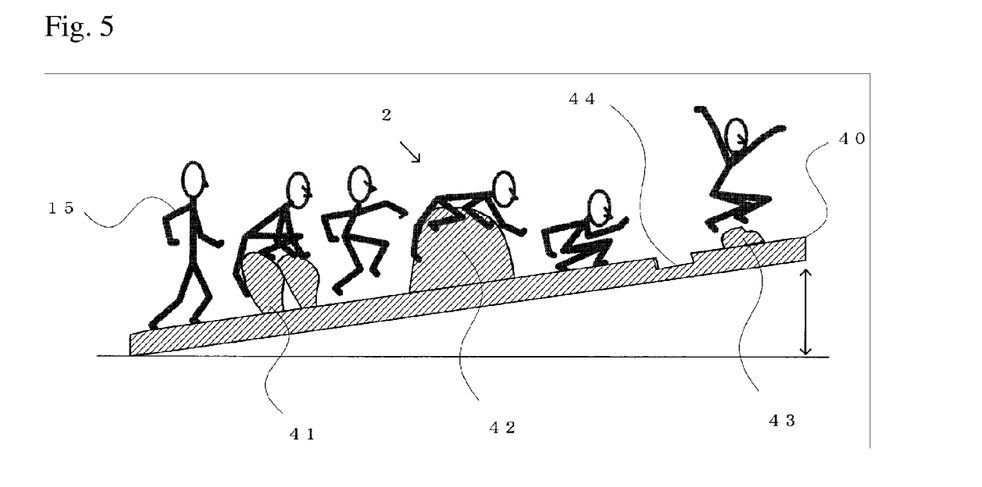
FIG. 5 is a longitudinal sectional view of the Climb of Grief exercise course of the present invention's system for measuring age on the basis of physical strength.
Figure 6:
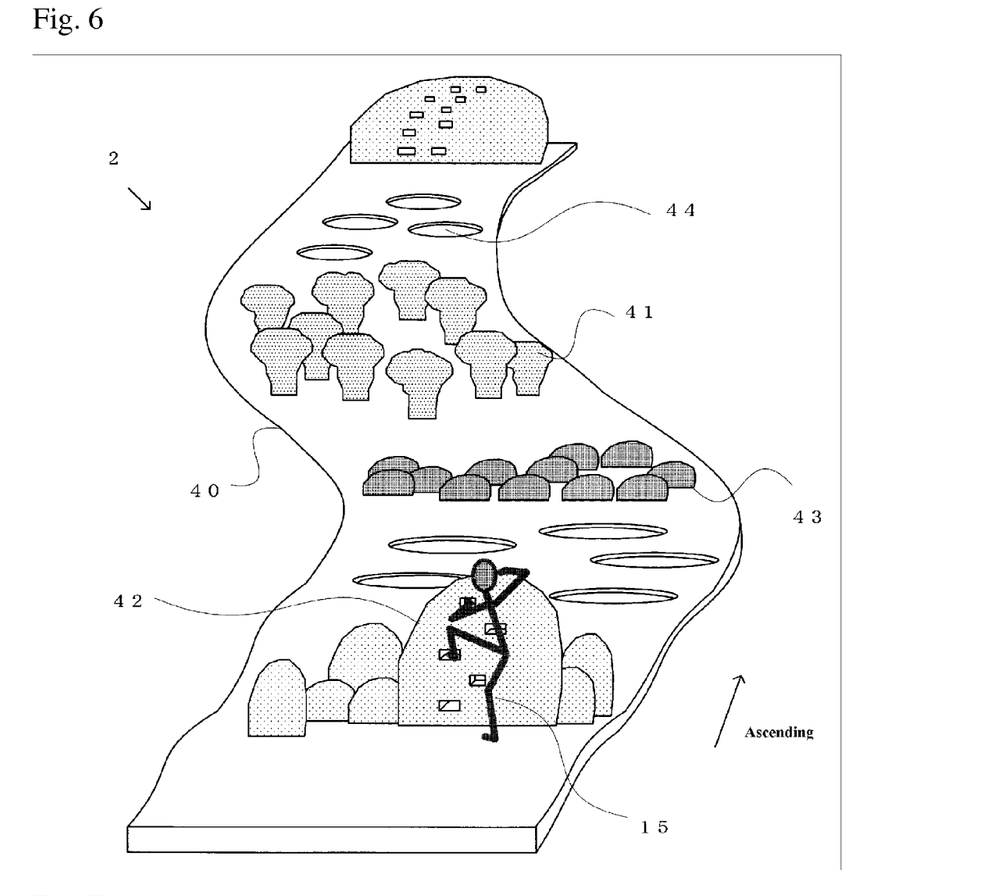
FIG. 6 is a perspective view of the Climb of Grief exercise course of the present invention's system for measuring age on the basis of physical strength.

FIG. 5 is a longitudinal sectional view of the Climb of Grief 2 exercise course. As shown in FIG. 5, this exercise course is a meandering, rising passageway 40 that is provided on a slope of a predetermined width and length. Obstacles 41 to 43 of various shapes and a hole 44 are provided on the climbing passageway 40. The user climbs up the obstacle 41 and jumps off from it. The user then crawls up the obstacle 42 and jumps down from it. The user then jumps over the hole 44 and the obstacle 43. Or, the user can climb up the passageway 40 and go around the obstacles and/or the hole, although by doing that the time needed to complete the course might become longer. FIG. 6 is a perspective view of Climb of Grief 2. The obstacles 41 to 43 are arranged along the passageway. If a user is not confident that he/she can climb up straight, he/she may advance up the passageway by detouring to the right or the left.

Figure 7:
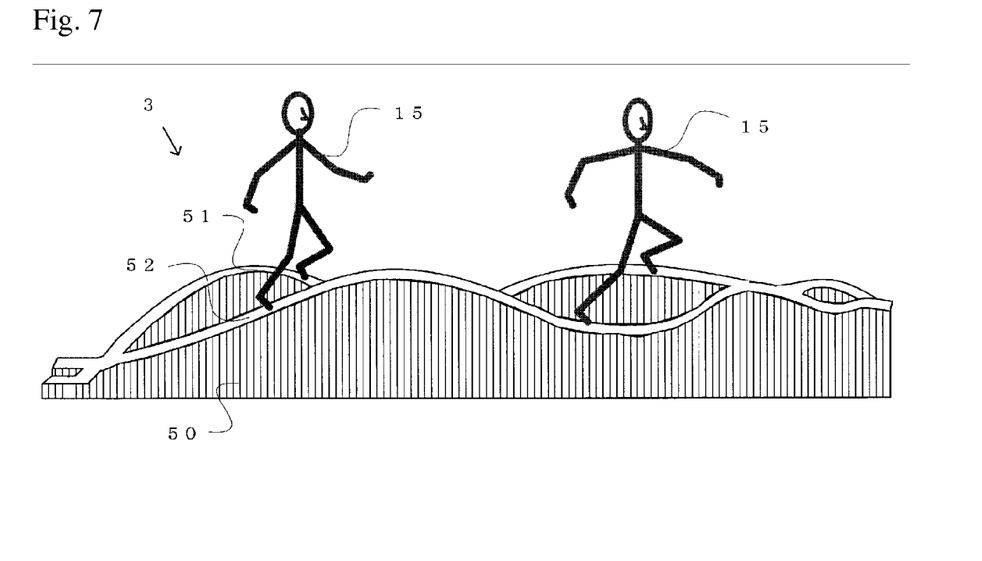
FIG. 7 is a perspective view of the Divided Pathway exercise course of the present invention's system for measuring age on the basis of physical strength.
Figure 8A:
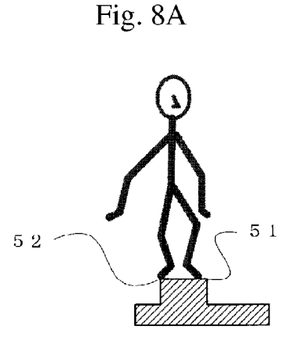
FIG. 8 is a cross sectional view showing variations in the walking surface(s) in the Divided Pathway exercise course of the present invention's system for measuring age on the basis of physical strength, with (a) showing a single walking surface, (b) and (c) showing two differently spaced walking surfaces, and (d), (e), and (f) showing three differently arranged pairs of walking surfaces that vary in terms of both the distance between the walking surfaces and the height of the two surfaces.
Figure 8B:
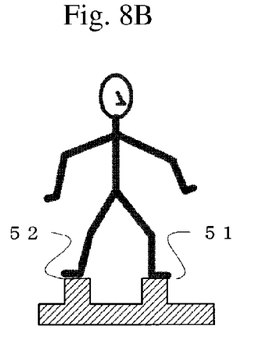
Figure 8C:
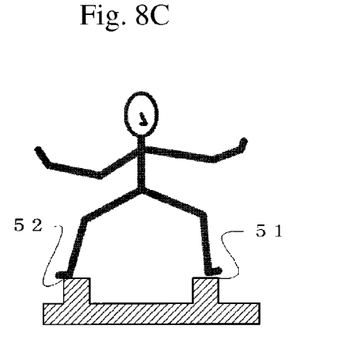
Figure 8D:
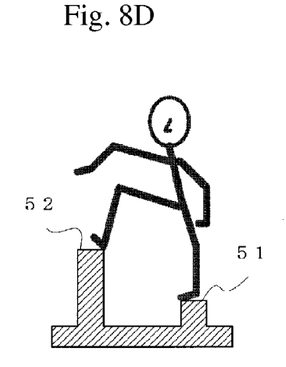
Figure 8E:
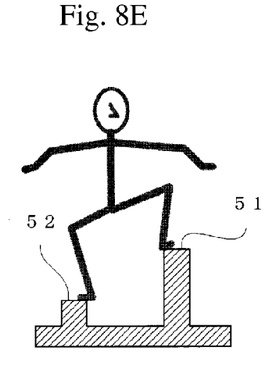
Figure 8F:
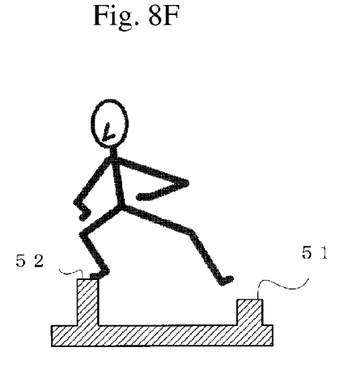

FIG. 7 is a perspective view of the Divided Pathway 3 exercise facility. This exercise course includes a passageway 50 that for most of its length is separated into two walking surfaces 51, 52, to be walked on, one for each foot of a user. Each of the two walking surfaces 51, 52 has a predetermined width, height, and length, and can have a high middle part, being inclined on both sides. The passageway 50 has a portion where it is divided into the two walking surfaces 51, 52, and also has a portion where the two walking surfaces 51, 52 converge into one again. Where the passageway is divided, the user walks with his/her legs apart. FIG. 8 is a cross sectional view showing the height of the two walking surfaces in Divided Pathway 3; (a) shows a portion where the two walking surfaces converge into one; (b) shows a portion where the passageway is divided into two walking surfaces; and (c) shows a portion where the distance between the two walking surfaces is large. The tops of the walking surfaces can have a high middle part and be inclined on both sides. This will make it difficult for a user to walk hurriedly on only one walking surface 51 or 52 instead of walking on both walking surfaces 51, 52 with his/her legs apart; (d), (e), and (f) show variations in the heights of, and distances between, the two walking surfaces. Such shapes of the walking surfaces result in an exercise that requires that a user frequently move the gravity center of his/her body from one side to the other.

Figure 9:
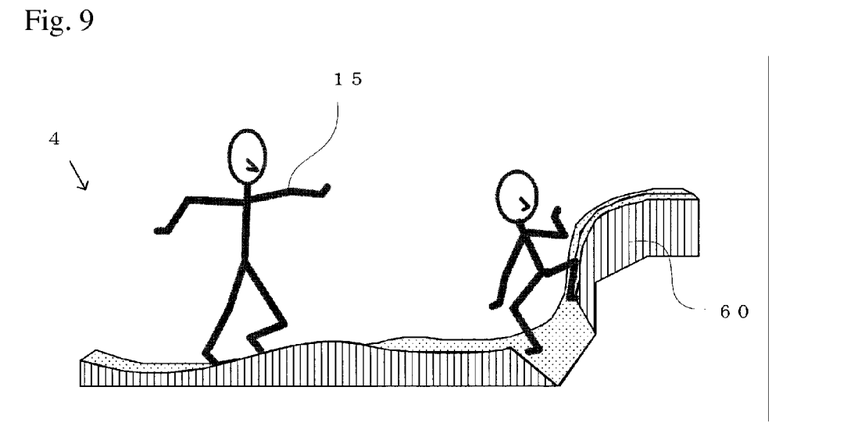
FIG. 9 is a perspective view of the Road of Torsion exercise course of the present invention's system for measuring age on the basis of physical strength.
Figure 10A:
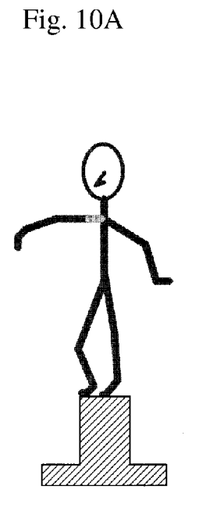
FIG. 10 is a cross sectional view of a connecting passageway 60 of the Road of Torsion exercise course of the present invention's system for measuring physical-strength age, with (a) to (d) showing variations in the walking surface.
Figure 10B:
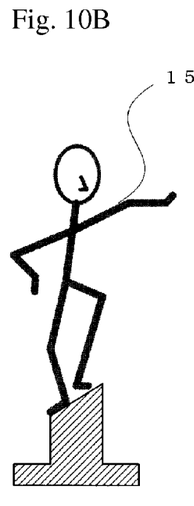
Figures 10C, 10D:
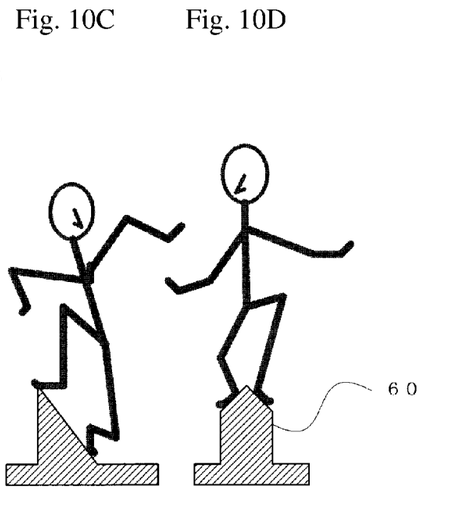

FIG. 9 is a perspective view of Road of Torsion 4. This exercise course includes one meandering passageway 60 of a predetermined width, height, and length, with the height of the passageway 60 varying along the way. FIG. 10 is a cross sectional view of the passageway 60 of Road of Torsion 4. The passageway 60 has a portion (a) where the walking surface is horizontal, a portion (b) where the walking surface inclines to one side, a portion (c) where the walking surface inclines to the other side, and a portion (d) where the walking surface inclines on both sides, separated by the centerline of the pathway.

Figure 11:
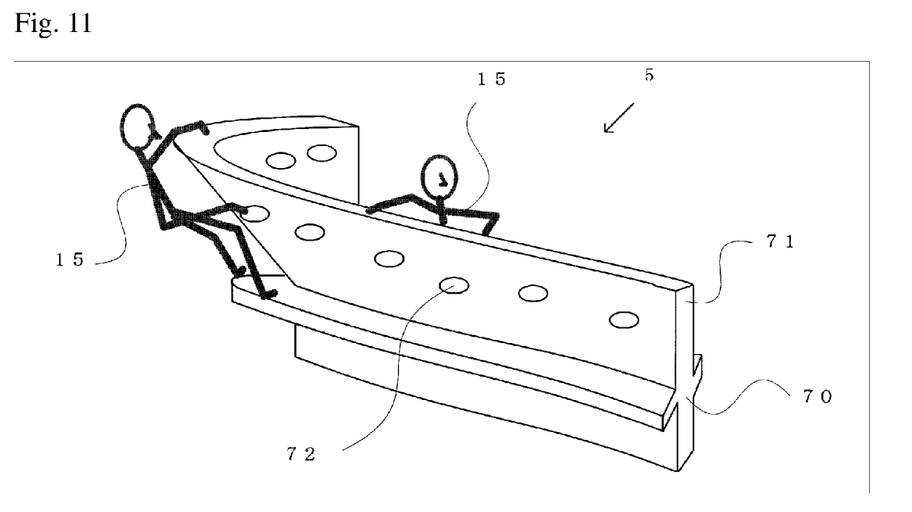
FIG. 11 is a perspective view of the Wall of Stagnation exercise course of the present invention's system for measuring age on the basis of physical strength.
Figure 12A:
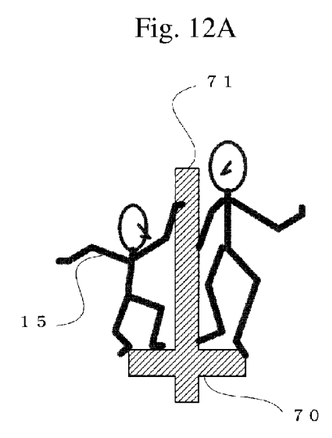
FIG. 12 is a cross sectional view of the Wall of Stagnation exercise course of the present invention's system for measuring age on the basis of physical strength, with (a) to (c) showing variations in the course's central wall.
Figure 12B:
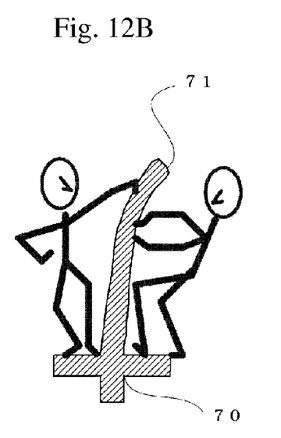
Figure 12C:
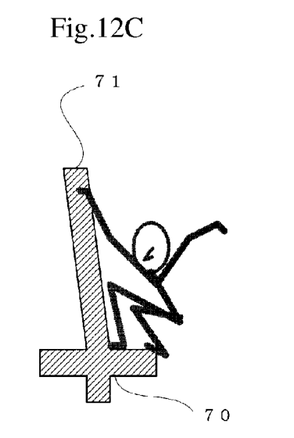

FIG. 11 is a perspective view of Wall of Stagnation 5. This exercise course includes a meandering passageway 70 that has a predetermined length, and a center wall 71 that divides the passageway 70 into two pathways. A large number of through-holes 72, into which a user can insert his/her hands to support his/her body, are provided in the central wall 71. FIG. 12 is a cross sectional view of Wall of Stagnation 5. The center wall 71 has an approximately perpendicular portion, as shown in (a); a curved portion, as shown in (b); and a portion that is inclined, as shown in (c). Therefore, a user needs to move forward inserting his/her hands into the through-holes 72 to support his/her body so as to not fall off the pathway; this requires arm-muscle strength. In addition, the pathway can be inclined.

Figure 13:
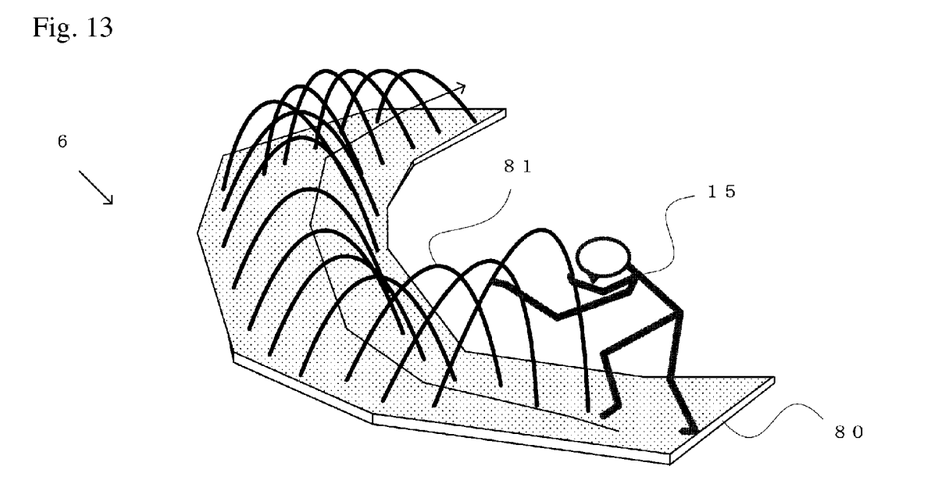
FIG. 13 is a perspective view of the Cave of Bones exercise course of the present invention's system for measuring age on the basis of physical strength.
Figure 14A:
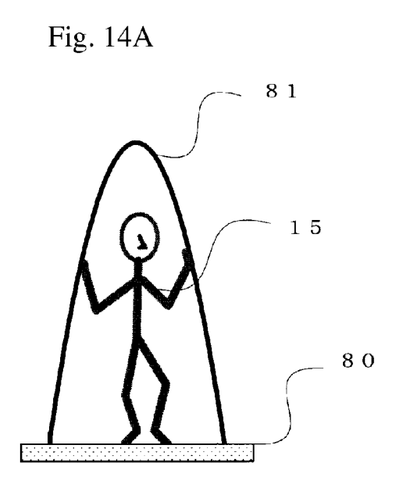
FIG. 14 is a cross sectional view of the tunnel-shaped passageway of the Cave of Bones exercise course of the present invention's system for measuring age on the basis of physical strength, with (a) to (d) showing variations in the sizes and shapes of the course's pipes.
Figure 14B:
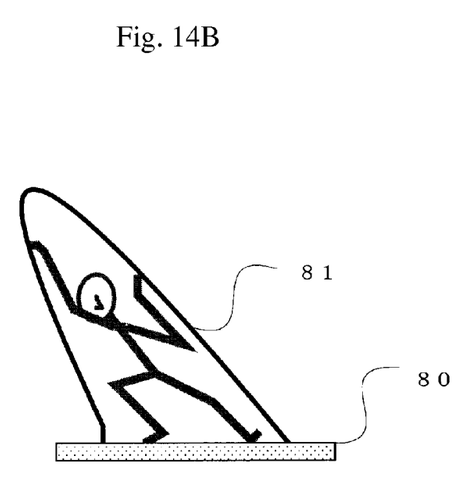
Figure 14C:
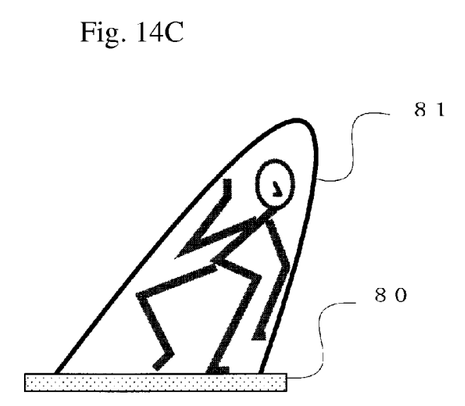
Figure 14D:
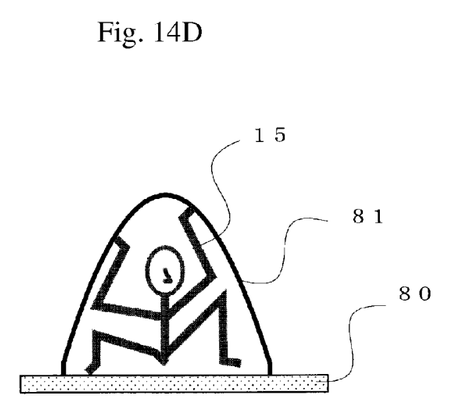

FIG. 13 is a perspective view of Cave of Bones 6. This exercise course includes a tunnel-shaped passageway 80, in which inverted-U-shaped pipes 81 of different heights are continuously arranged at predetermined intervals. FIG. 14 includes four cross sectional views of the tunnel-shaped passageway 80. The passageway has a portion (a) where the user can walk while standing erect; portions (b) and (c) where the user must lean to the right or left in order to move forward, because the pipes 81 are inclined; a portion (d) where the user must sit down on his/her heels or crouch in order to move forward; and a portion (not shown) where the user must walk with a stoop in order to move forward.

Figure 15:
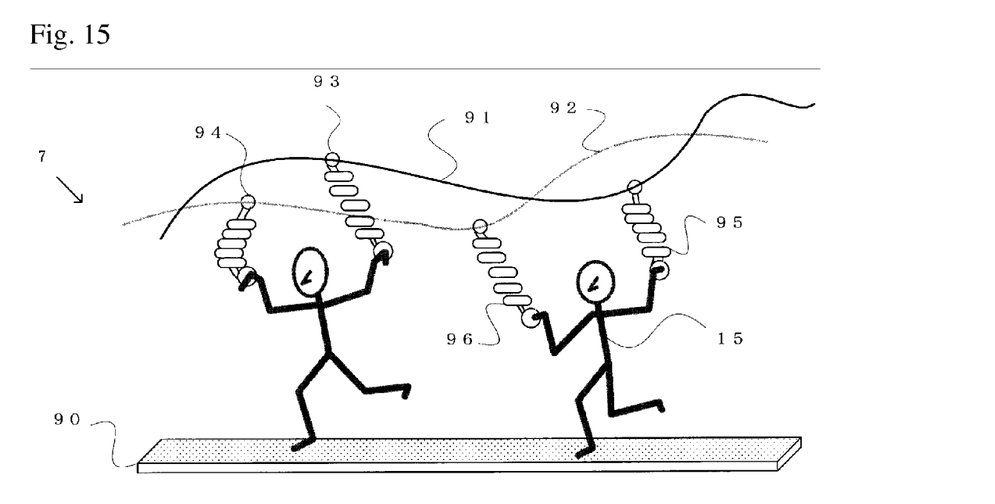
FIG. 15 is a perspective view of the Stretch with Hanging Rings exercise course of the present invention's system for measuring age on the basis of physical strength.
Figures 16A, 16B:
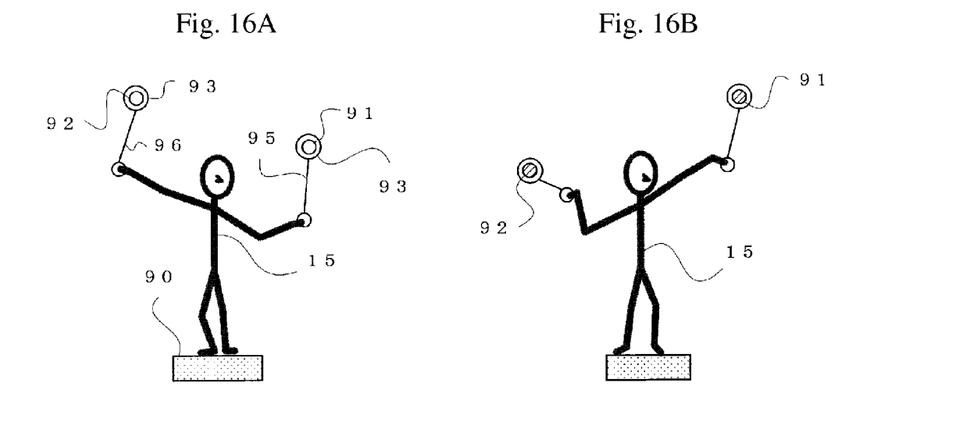
FIG. 16 shows variations in the positioning of the arms of a user 15 according to variations in the rails of the Stretch with Hanging Rings exercise course of the present invention's system for measuring age on the basis of physical strength.
Figure 16C:
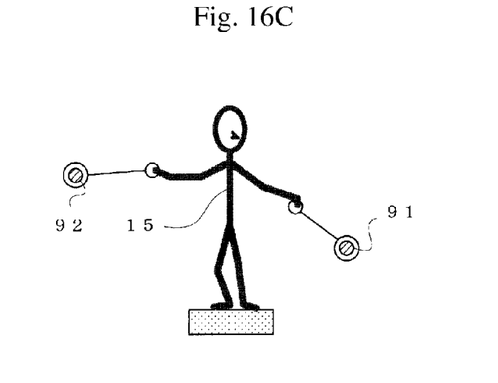
Figure 16D:
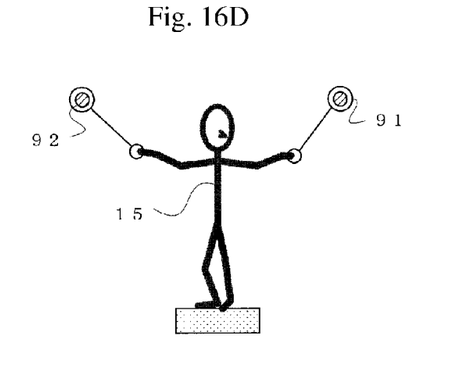

FIG. 15 is a perspective view of Stretch with Hanging Rings 7. This exercise course includes: (1) a passageway 90 that has a predetermined length; (2) two rails 91, 92 that meander up and down and to the right and left; (3) multiple metal fittings 93, 94 that are mounted to the rails and slide forward and backward, and (4) two interconnected series of hanging-rings 95, 96 that are connected with the metal fittings 93, 94, respectively, and that as a group expand and contract in an accordion-like fashion. FIG. 16 shows variations in the positions of the arms of a user 15 depending on the positions of the rails 91, 92. In (a) and (b), one or the other of the user's arms is raised upward; in (c), both arms are extended downward to be slanted off the horizontal; and in (d), both arms are raised to be slanted off the horizontal; the rings can be arranged so that a user's arms are positioned in other ways.

Figure 17:
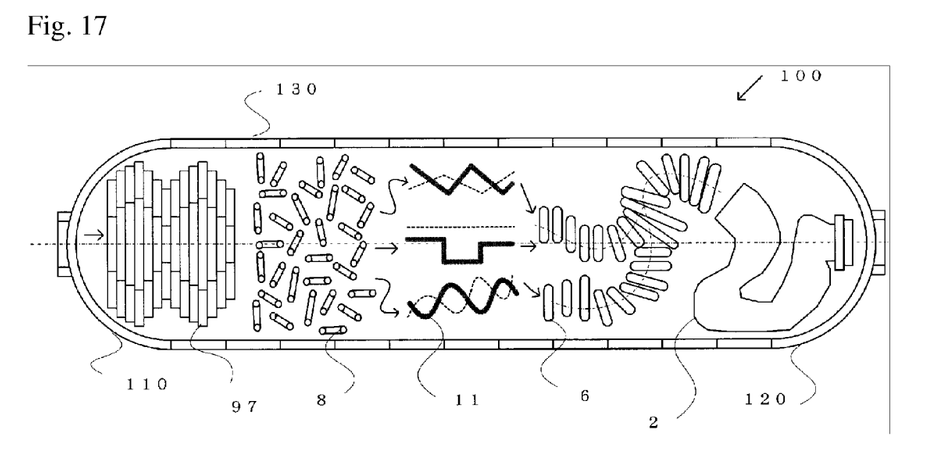
FIG. 17 is a plane view showing the arrangement of the exercise courses of the present invention when they are accommodated in a long dome.
Figure 18:
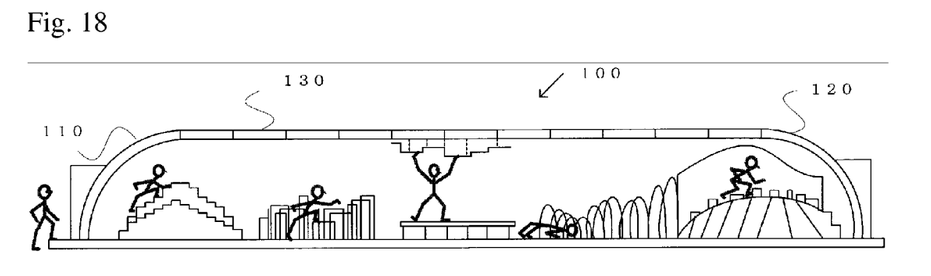
FIG. 18 is a longitudinal sectional view showing the arrangement of exercise facilities when the exercising courses of the present invention are accommodated in a long dome.

FIG. 17 is a plane view showing the exercise courses accommodated in a long dome. FIG. 18 is a longitudinal sectional view of the inside of the long dome 100 in which the exercise courses are accommodated. As shown in FIGS. 17 and 18, the long dome 100 includes front and rear portions which are divided into halves of a hemisphere doom respectively and an intermediate portion includes multiple arches 130 between the front portion and the rear portion, and has an entrance 110 and an exit 120 at its front and rear portions, respectively. The length of the long dome 100 can be extended by adding more arches 130 thereto. Also, if there are a large number of exercise courses, some long domes 100 can be combined together to accommodate the exercise courses.

It is preferable that such a long dome 100 be made of polystyrene foam. Thus, this long dome has the merit of being easy to construct, its service life will be long, and it is inexpensive to construct. Also, many skylights and bay windows can be arranged in the long dome, so that the inside of the long dome will be well-lit, bright, and give users a feeling of freedom. As one example, the following are arranged inside the long dome 100: Staircases 97, having different gradients; Pipeline 8 where a large number of gate-type, squarely bent pipes are crowded together; Road of Reaching Out 11, where the users stretch their arms to grab bars arranged on the ceiling and walk sideways in a narrow passageway; Cave of Bones 6, where the users move forward passing through curved, pipe-like tunnels; and Climb of Grief 2, where the users climb up a slope having many obstacles.

The present invention's system for measuring a user's age on the basis of the user's physical strength—which includes various types of exercise courses that may have in them some elements of amusement—can be installed at a recreational facility or the like, and can be mass-produced.

It will be readily seen by one of ordinary skill in the art that the present invention fulfills all of the objects set forth above. After reading the foregoing specification, one of ordinary skill will be able to affect various changes, substitutions of equivalents and various other aspects of the invention as broadly disclosed herein. It is therefore intended that the protection granted hereon be limited only by the definition contained in the appended claims and equivalents thereof.

What is claimed is:

1. A system for measuring a user's age on a basis of the user's physical strength, comprising multiple exercise courses that include various types of exercise-related devices/features, with the exercise courses structured such that
   a user is tested on a variety of physical abilities, including: muscle strength in multiple parts of his/her body, flexibility of the body, balance of the body, and agility of the body,
   the extent to which a user utilizes each of his/her various physical abilities forms an index of the amount of exercise performed, and
   the combination of the values of the indexes for each exercise course is different from the combination of values of indexes in each of the other exercise courses;
   the user's age on the basis of the physical strength is calculated based on the amount of time that the user takes to complete all of the exercise courses; and
   each of the various exercising abilities of the user is assessed based on the amount time that the user takes to complete each of the courses.

2. The system for measuring age on a basis of physical strength according to claim 1, wherein the exercise courses are structured such that the specific exercises within each exercise course are arranged so that a user needs to memorize their order and specific features, and to use his/her judgment in selecting the posture or route to be taken in performing each exercise, with the result that intelligence is one of the indexes.

3. The system for measuring age on a basis of physical strength according to claim 1, wherein the exercise course is equipped with
   a passageway such that multiple logs having flat upper faces are horizontally or diagonally installed at predetermined heights above the ground (floor), and
   a structure, arranged in the middle of the passageway, that has a low ceiling that requires a user to change from a standing-upright posture to bending-down posture, a squatting posture, or an on-all-fours posture.

4. The system for measuring age on a basis of physical strength according to claim 1, wherein
   the exercise course is a meandering, upward-sloped passageway having a predetermined width and length, and
   multiple projections or holes are provided on said passageway so as to make a user do one or more of the following: climbing up and jumping down; jumping over; crawling up and running down; or climbing while avoiding obstacles.

5. The system for measuring age on a basis of physical strength according to claim 1, wherein
   the exercise course consists of a passageway that for most of its length consists of two separate surfaces to be walked on (hereinafter "walking surfaces"), one for each of a user's legs, with each walking surface having a predetermined width, height, and length, and with the passageway such that in some portions one walking surface is higher than the other;
   the passageway has one or more portions where the two walking surfaces are separated from each other (separated-walking-surfaces portion(s)), and one or more portions where the two walking surfaces converge into one (united-walking-surfaces portion(s)); and,
   the separated-walking-surfaces portion(s) include one or more sections where the user can or must walk with his/her legs wide apart, as well as one or more sections where the two walking surfaces are of different heights, and one or more sections where the two walking surfaces have the same height.

6. The system for measuring age on a basis of physical strength according to claim 1, wherein the exercise course consists of one passageway having a predetermined width, height, and length, and with the passageway arranged so that
   it is winding from beginning to end; and
   it includes a portion where the walking surface goes up and down, a portion where the walking surface is horizontal, a portion where the walking surface is inclined to one side, and a portion where the walking surface is inclined on both sides, with the center of the walking surface being a boundary between the two sides.

7. The system for measuring age on a basis of physical strength according to claim 1, wherein
   said exercise course is a meandering passageway having a predetermined length and a center wall that divides the passageway into two pathways, with said central wall provided with multiple through-holes into which a user can insert his arms so as to support his/her body, and
   having an approximately vertical portion, an inclined portion, and a portion that is curved on both side faces.

8. The system for measuring age on a basis of physical strength according to claim 1, wherein the exercise course consists of a tunnel-shaped passageway in which inverted-U-shaped pipes are continuously arranged at predetermined intervals;

pipes of different height are used so that the passageway has a portion in which the user can walk upright, a portion in which the user must bend down in order to move forward, and a portion in which a user must crouch in order to move forward; and the pipes incline to the right or left so that the passageway has one or more portions where a user must bend to the right or left in order to move forward.

9. The system for measuring age on a basis of physical strength according to claim 1, wherein the exercise course is a passageway of a predetermined length, and is arranged such that meanders up and down and to the right and left, and is equipped with two rails, one on the passageway's right side and one on the left side, with the rails arranged so that they sometimes are inclined upward and sometimes inclined downward, and sometimes are directed to the left and sometimes to the right metal fittings that are mounted to the rails and that slide forward and backward, and an interconnected series of hanging rings that are connected to the metal fittings.

10. The system for measuring age on a basis of physical strength according to claim 1, wherein said exercise courses are accommodated in a long dome made of polystyrene foam.

* * * * *